(12) United States Patent
Landolt et al.

(10) Patent No.: US 6,344,191 B2
(45) Date of Patent: Feb. 5, 2002

(54) CHEMICAL ATTRACTANTS FOR MOTHS

(75) Inventors: Peter J. Landolt, Yakima, WA (US); Robert R. Heath, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/737,532

(22) Filed: Dec. 14, 2000

Related U.S. Application Data

(62) Division of application No. 09/156,348, filed on Sep. 18, 1998, now Pat. No. 6,190,653.

(51) Int. Cl.$^7$ ........................ A01N 25/00; A01N 31/00; A01N 33/00; A01N 37/00
(52) U.S. Cl. ............................. 424/84; 43/107; 43/131; 43/132.1; 43/133; 424/405; 424/719; 514/557; 514/724; 514/740; 514/957
(58) Field of Search ......................... 424/84, 405, 719; 43/107, 132.1, 131, 133; 514/557, 724, 740, 957

(56) References Cited

U.S. PATENT DOCUMENTS 3,930,042 A  * 12/1975 Dunnet ........................ 426/475
5,656,260 A      8/1997 Boden et al. ................. 424/84

OTHER PUBLICATIONS

Rosario et al., 'Comparison of headspace volatiles from winged beans and soybeans', J. Agric. Food Chem. (1984), vol. 32, pp. 1011–1015.*

Benn et al., 'Characterization of tequila flavor by instrumental and sensory analysis', J. Agric. Food Chem. (1996), vol. 44, pp. 557–566.*

K. F. Haynes, J.Z. Zhao and A. Latif, "Identification of Floral Compounds from *Abelia grandiflora* that Stimulate Upwind Flight in Cabbage Looper Moths," *Journal of Chemical Ecology* (1991) 17:637–646.

P.J. Landolt, B. Lenczewski and R.R. Heath, "Lure and Toxicant System for the Cabbage Looper (Lepidoptera: Noctuidae)," *Journal of Economic Entomology* (1991) 84:1344–1347.

S.W. Frost, "Continued Studies of Baits for Oriental Fruit Moth," *Journal of Economic Entomology* (1928) 21:339–348.

R.R. Heath, P.J. Landolt, B. Dueben, and B. Lenczewshi, "Identification of Floral Compounds of Night–Blooming Jessamine Attractive to Cabbage Looper Moths," *Environ. Entomol.* (1992) 21:854–859.

M. J. Norris, "The Feeding–Habits of the Adult Lepidoptera Heteroneura," Transactions of the Royal Entomological Society of London (1936) 85:61–90.

P.J. Landolt and E.R. Mitchell, "Attraction of Tobacco Budworm Moths (Lepidoptera: Noctuidae) to Jaggery, A Palm Sugar Extract," *Florida Entomologist* (1997) 80:402–407.

P.J. Landolt, "Attraction of Mocis Latipes (Lepidoptera: Noctuidae) to Sweet Baits in Traps," *Florida Entomologist* (1995) 78:523–530.

A.B. Demilo, C–J Lee, D.S. Moreno and A.J. Martinez, "Identification Volastiles Derived from *Citrobacter freundii* Fermentation of a Trypticase Soy Broth," *Journal of Agricultural and Food Chemistry* (1996) 44:607–612.

N.D. Epsky et al., "Identification of Volative Chemicals from Enterobacter Agglomerans (Enterobacteriaceae) that are Attractive to Anastrepha Suspensa (Diptera: Tephritidae)," *1997 Annual Report*, USDA,ARS, (Jan. 1998) Gainesville, Fl.

D.C. Robacker and R.J. Bartelt, "Chemicals Attractive to Mexican Fruit Fly from *Klebsiella pneumonia* and *Citrobacter fruendii* Cultures sampled by Solid–Phase Microextraction," *Journal of Chemical Ecology* (1997) 23:2897–2915.

D.C. Robacker, D.S. Moreno and A.B. Demilo, "Attractiveness to Mexican Fruit Flies of Combinations of Acetic Acid with Ammonium/Amino Attractants with Emphasis on Effects of Hunger," *Journal of Chemical Ecology* (1996) 22:499–511.

P. Utiro and K. Erikson, "Volatile fermentation products as attractants for Macrolepidoptera," *Ann. Zool. Fenn.*, (1977) 14(2):98–104.

V.G. Dethier, "Chemical Insect Attractants and Repellents," *The Blakiston Company*, Chicago, IL, (1947) Chapter 4, pp. 75–102.

* cited by examiner

*Primary Examiner*—Jose'G. Dees
*Assistant Examiner*—Frank Choi
(74) *Attorney, Agent, or Firm*—Margaret A. Connor; M. Howard Silverstein; John D. Fado

(57) ABSTRACT

Compositions and lures are described which provide synthetic chemical attractants which function as highly effective attractants for male and female moths, primarily moths of the family Noctuidae. In one aspect, the attractants provide an effective attractant amount of vapor of 3-methyl-1-butanol, 3-methyl-1-pentanol or mixtures thereof. In another aspect, the attractants provide vapor blends of acetic acid and one or more compounds selected from the group consisting of 3-methyl-1-butanol, 3-methyl-2-butanol, and 3-methyl-1-pentanol. By attracting male and female moths to traps or baits, the chemical attractants provide a means for detecting, surveying, monitoring, and controlling the moths.

11 Claims, 6 Drawing Sheets

CHEMICAL ATTRACTANTS FOR MOTHS

CROSS-REFERENCE TO RELATED APPLICATIONS

This application is a division of U.S. patent application Ser. No. 09/156,348, filed Sep. 18, 1998 now U.S. Pat. No. 6,190,653.

BACKGROUND OF THE INVENTION

1. Field of the Invention

The present invention relates to synthetic chemical insect attractants. More particularly, the invention relates to chemical attractants and use thereof to detect, survey, monitor, and/or control moths (Lepidoptera).

2. Description of the Art

Many species of moths (Lepidoptera) are pestiferous. Larvae or caterpillars of a number of species of moths are serious pests of agricultural crops throughout the world. In the family Noctuidae, in particular, are many species of cutworms, armyworms, fruitworms, and others that cause severe losses of vegetable and fruit, as well as forage, and fiber crops and necessitate the use of large amounts of pesticides to reduce these losses. Three important species in western North America are the bertha armyworm (*Mamestra configurata*), the spotted cutworm (*Xestia c-nigrum*), and *Lacanobia subjuncta*. These are pests of many vegetable and forage crops, and *Lacanobia subjuncta* has recently been identified as a serious pest of apple.

Efforts to control pest moth populations on agricultural crops have relied heavily on broadcast applications of pesticides which are under increasing regulatory pressure. Chemical attractants are widely used to monitor the emergence patterns and distributions of moths on crops. These are exclusively sex pheromones attractive solely to males. They are of limited use in pest control because of the lack of effect on females and because they are not effective as attractants when the same sex pheromones are used for mating disruption by air permeation. The development of chemical attractants for monitoring pest levels and economic injury levels of pest moths on crops has been hampered by a lack of effective lures for females of these species. Similarly, the development of control technologies involving mass trapping of moths or poison baits would be greatly facilitated by the availability of effective lures for females of pest species.

Numerous species of Lepidoptera, including pest species of moths, are attracted to fermented sweet baits. Fermented sweet baits have long been used by collectors of moths and butterflies (W. J. Holland, *The Moth Book. A Guide to the Moths of North America*, Dover Publishing, Inc., New York, N.Y., 1903, 479 pages; T. D. Sargent, Legion of Night. *The Underwing Moths*, Massachusetts Press, Amherst, Mass., 1976, 22 pages). Lepidoptera and other insects are attracted to natural sources of sugars such as fruits, tree sap, insect honeydew, and plant nectars (M. J. Norris, *Trans. Royl. Entomol. Soc. London* 85:61–90 (1935)). It is generally considered that such materials must be fermented by microbes to become attractive, possibly due to the generation of specific odorants by colonizing bacteria and fungi (Norris, supra; P. J. Landolt, *Florida Entomologist* 78:523–530 (1995)). Attraction of pestiferous species of Lepidoptera to such materials has been documented for possible use in pest control, and include several species of Noctuidae (cutworm and armyworm family). These are the corn earworm (L. P. Ditman and E. M. Cory, *Journal of Economic Entomology* 26:109–115 (1933)), grass loopers (Landolt, 1995, supra), and the tobacco budworm (P. J. Landolt and E. R. Mitchell, *Florida Entomologist* 80:403–407 (1997)). Large numbers of noctuids were captured in traps baited with solutions of molasses or syrups by W. W. Frost (*Journal of Economic Entomology* 21:339–348 (1928)) who did not identify them to species. Isolation and identification of the odorants from fermented sweet baits that are attractive to moths would provide a useful attractant for use in monitoring and controlling pest species of Lepidoptera on agricultural crops.

Although numerous synthetic chemical attractants are known for moths, none are based on moth attraction to fermented sweet baits and very few are effective in attracting females. Most synthetic chemical attractants for moths are female-produced sex pheromones attractive to males (M. S. Mayer and J. R. McLaughlin, *Handbook of Insect Pheromones and Sex Attractants*, CRC Press, Boca Raton, Fla., 1991, 1083 pages). Several chemicals have also been identified from floral volatiles that are attractive to both sexes of some moth species (primarily Plusiinae) that obtain nectars from certain flowers. These are phenylacetaldehyde, benzaldehyde, benzyl acetate, 2-phenylethanol, and benzyl alcohol (W. W. Cantelo and M. Jacobson, *Environmental Entomology* 8:444–447 (1979), K. F. Haynes et al., *Journal of Chemical Ecology* 17:637–646 (1991), R. R. Heath et al., *Environmental Entomology* 21:854–859 (1992), C. E. Smith et al., *Journal of Economic Entomology* 36:619–621 (1943), M. Jacobson et al. *Experientia* 32:964–966 (1976)).

The bertha armyworm, *Mamestra configurata*, is a pest of numerous crops, including alfalfa, flax, and canola (P. G. Mason et al., *Can. Entomol.* 130:321–336 (1998)). It is broadly distributed in North America. The spotted cutworm *Xestia c-nigrum* also is a pest of numerous crops, primarily vegetable crops (J. F. Howell, *Environmental Entomology* 8:1065–1069 (1979)) and is widely distributed in North America. *Lacanobia subjuncta* is a recent and serious pest of apple in the Pacific Northwest (P. J. Landolt, *Pan-Pacific Entolomol.* 74:32–38 (1998)) and is found across the temperate zone of North America. Numerous other species of noctuid moths are pests of nearly all agricultural crops throughout the world.

SUMMARY OF THE INVENTION

The present invention is directed to chemical attractants for male and female moths. In one aspect, the invention is directed to attracting noctuid moths using an effective attractant amount of vapors of 3-methyl-1-butanol or 3-methyl-1-pentanol or mixtures thereof as a means for detecting, surveying, monitoring, and controlling moths.

In another aspect, the invention is directed to attracting noctuid moths using an attractant chemical combination to provide an effective attractant amount of vapor blends or vapor mixtures of (I) acetic acid and (II) one or more compounds selected from the group consisting of 3-methyl-1-butanol (isoamyl alcohol), 3-methyl-2-butanol, and 3-methyl-1-pentanol. The volatilized blends or mixtures function as highly effective attractants for noctuid moths, and provide a means of detecting, surveying, monitoring, and controlling pest species of moths.

In one embodiment, the volatilized blend of the attractant combination is provided by a mixture of I and II. In another embodiment, the vapor blend is provided by a combination of I and II wherein I and II are positioned in sufficient proximity to one another to form a volatilized blend. In still a further embodiment, the vapor blend is provided by a single chemical, e.g., 3-methylbutyl acetate which releases a vapor blend of acetic acid and 3-methyl-1-butanol into the atmosphere.

The attractants of the invention yield specific attractants for noctuid moths, and provides a means for detecting, surveying, monitoring, and controlling these pests.

The attractants of the invention are the first known chemical attractants that are broadly attractive for female noctuid moths. Thus, the chemical attractants of the invention provide the first means of monitoring females of pest moth species, for the purpose of optimizing the timing of control procedures and for assessing population densities. The attractants are also useful in devising control strategies for pest moths through the combination of attractants with toxicants to kill female moths. Because the invention results in the trapping or death of female moths, it directly removes reproductive potential from the field, effectively reducing potential populations of pest moths and saving crops from damage.

Exemplary of noctuid moth species are *Mamestra configurata*, *Xestia c-nigrum*, and *Lacanobia subjuncta*, which are found throughout much of North America.

Without being bound by theory, it is believed that the moth orientation to sweet food materials is the bases for their response to the attractants of the invention, thus foraging moths are likely to be lured by the attractants of the invention. In use, an effective attractant amount of the attractants of the invention is provided in an area where moths are to be attracted, that is, an area frequented by noctuid moths of interest; an area where noctuid moths may forage for food or otherwise occur; or selected areas where detecting, surveying, monitoring, and/or controlling of these pests is desired. Conveniently, 3-methyl-1-butanol, 3-methyl-1-pentanol or mixtures thereof or I and II are dispensed within a trapping means to attract and trap the moths.

The chemical attractants of the invention are superior to non-chemical baits, e.g., molasses, jaggery, jams, sugar solutions, and fruit purees, because they provide a predictable, stable, and long lasting source of attractiveness.

The invention is also directed to lures wherein 3-methyl-1-butanol or 3-methyl-1-pentanol or mixtures thereof are in a dispenser means which releases the chemical or mixture as a vapor. Additionally, the invention is directed to lures wherein the attractant combination of I and II are held in a dispenser means which releases I and II so as to form the attractant vapor blend.

The invention is also directed to trapping systems for trapping noctuid moths. Such systems include trapping means, and an effective attractant amount of the attractant compounds, mixtures or combination of the invention. A preferred trap for the attractant combination of the invention is one which has a chamber wherein vapors of I and II form a blend such that the vapor blend of I and II exits the trap chamber and attracts moths to the chamber where they are trapped.

The invention is also directed to a packaged attractant and kit for attracting noctuid moths which include the compounds, mixtures or combination of components I and II.

Many species of noctuid moths are key pests of agricultural crops and cause losses of vegetable, fruit, forage, and fiber crops through direct consumption by larvae and by reduction in food quality. The attractants of the invention are useful to remove such moths in areas where they are reproducing and causing damage to crops and commodities.

The chemical attractants of the invention provide a means of reducing populations of pestiferous species over defined areas by mass trapping and alleviate threats of losses to agricultural crops. Further, when used in combination with a control agent for the moths, such as a drowning solution, a pesticide or biological control agent, the composition can be used as a direct control agent.

The attractants of the invention can also be used as a poisoned bait by combining them with feeding stimulants and toxicants that the moths ingests, effectively killing or sterilizing them.

In sum, the novel chemical attractants of the invention provide a tool for the detection of noctuid moth species and provide a means for population control and population density estimation of these pests. The lures and trapping systems which include the attractants of the invention are useful for farmers and growers, orchardists, homeowners and gardeners, and other users where control of pest noctuid moths is desired.

The utility and effectiveness of the invention in attracting noctuid moths suggests the following applications: (1) the detection of populations, (2) the detection of population outbreaks or rapid population buildups, (3) the monitoring of populations, (4) the control of problem populations in discrete areas. In certain geographic areas there is a need to detect the presence of certain species of pest moths as they move into new areas, so that these populations may be destroyed or controlled. Many species of armyworms and cutworms are prone to intermittent population outbreaks in some geographic areas, causing severe losses to agricultural crops. Such outbreaks can be detected by programs to attract and trap moths, thereby gaining information on changes in moth numbers. It is expected that a means of sampling females of a species, rather than males, will provide more valuable information more closely related to pest activity and reproduction at a site. The attractants of the invention are also useful as a bait for traps used to monitor changes in population level. For example, efficacy of control procedures such as pesticide or microbial applications, may be measured with attractant traps that indicate population levels. Again, it is expected that a means of sampling females rather than exclusively males will provide more useful information in relation to the population of a pest at a discrete site. The attractants are also useful to control moth populations and activities where they are a problem through a variety of approaches, including localized trapping out of moths, and the use of the attractant in a poison bait formulation to kill attracted moths.

In accordance with this discovery, it is an object of the invention to provide chemical attractants for male and female moths, particularly noctuid moths.

Another object of the invention is the provision of the attractants as detection, surveying, monitoring, or control agents for moths.

A further object of the invention is the provision of the attractants of the invention for use with control agents, including drowning solutions, insecticides, biological control agents, or other toxicants, to attract and combat these pests.

Another object of the invention is the provision of effective methods of monitoring or controlling pest moths using the chemical attractants of the invention.

A further object of the invention is the provision of trapping systems for trapping pest moths which include trapping means and an effective attractant amount of the attractant combination of the invention.

A still further object of the invention is the provision of kits which include the compounds, mixtures or combination of components required to produce the attractants of the invention.

Other objects and advantages of the invention will become readily apparent from the ensuing description.

DETAILED DESCRIPTION OF THE INVENTION

Figure 1A:
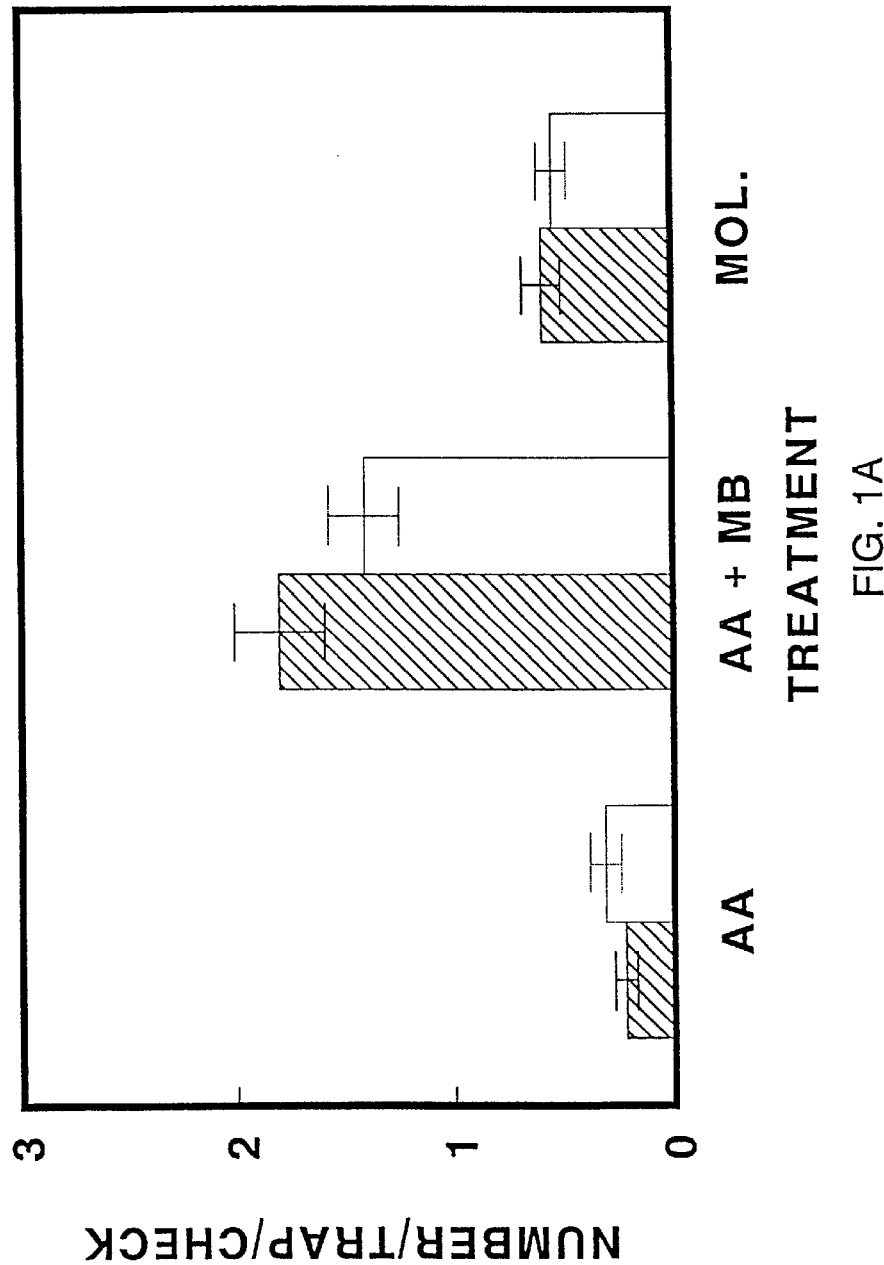
FIG. 1 shows the mean numbers of *Lacanobia subjuncta* (FIG. 1A), *Mamestra configurata* (FIG. 1B), and *Xestia c-nigrum* (FIG. 1C) moths captured in traps baited either with acetic acid alone (AA), with the combination of acetic acid and 3-methyl-1-butanol (AA+MB) or with fermented 10% molasses solution (MOL.).

This invention comprises specific attractants for male and female moths of the family Noctuidae, and provides a means for detecting, surveying, monitoring, and controlling these moths. In particular, the attractants of the invention find particular use for detecting, surveying, monitoring, and controlling pestiferous noctuid species. In one aspect of the invention, the synthetic attractant composition of the invention comprises 3-methyl-1-butanol, 3-methyl-1-pentanol or mixtures thereof, in an effective attractant amount. Attracted moths respond to the vapor of the individual compounds or mixtures in air and they move upwind towards the attractant source. An effective amount of an attractant vapor is defined as that quantity of the compound or compounds that attracts moths to the location of the compound or compounds at a rate higher than moths are attracted to a location devoid of the attractant. An effective attractant amount is determined as the quantity of the compound or compounds emitted from a formulation or dispenser holding the attractant compound or compounds that is sufficient to elicit an attraction response from moths downwind of the attractant.

In another aspect of the invention, the composition of the invention is an attractant chemical combination which comprises a vapor blend or vapor mixture of vapor of (I) acetic acid and vapor of (II) one or more compounds selected from the group consisting of 3-methyl-1-butanol, 3-methyl-2-butanol, and 3-methyl-1-pentanol, in an effective attractant amount.

Attracted moths respond to the combination of odorants from I and II present simultaneously in air and they move upwind towards the source of the blend. An effective amount of an attractant vapor blend of I and II is defined as that quantity of the chemical blend that attracts moths to the location of the blend at a rate higher than moths are attracted to a location devoid of the blend. An effective attractant amount is determined as the quantities of the compounds emitted from a formulation or dispenser holding the compounds that is sufficient to elicit an attraction response from moths downwind of the attractant vapor blend or mixture.

The attractant vapor composition of the combination may be provided by (a) a mixture of I and II; (b) a combination of I and II wherein I and II are positioned in sufficient proximity to each other effective to form a volatilized blend of I and II; or (c) a single compound, e.g., 3-methylbutyl acetate which dissociates into a vapor blend of I and II, e.g., a vapor blend of acetic acid and 3-methyl-1-butanol. In all cases, whether I and II are formulated or presented separately or together, I and II are provided so as to provide an effective attractant amount of the odor blend of I and II.

All of the compounds for producing the vapor composition of the invention are commercially available. Acetic acid vapor is provided by compounds that produce volatilized acetic acid, for example, aqueous acetic acid, glacial (concentrated) acetic acid or ammonium acetate. Component II vapor is provided by compounds 3-methyl-1-butanol, 3-methyl-2-butanol, and 3-methyl-1-pentanol. A vapor blend of acetic acid and isobutanol may be also provided by 3-methylbutyl acetate which dissociates to form a volatilized blend of acetic acid and 3-methyl-1-butanol. All of the foregoing compounds are liquid over the range of temperature at which moths actively forage in nature, which is about 5 to 30° C., with most activity of concern occurring from about 10 to 25° C.

Lures. It is envisioned that the chemical attractants of the invention would be useful in detecting, surveying, monitoring, or controlling noctuid moth populations when used as a lure. A lure includes a dispenser means which contains a chemical or chemicals which provide the attractant. For purposes of this invention, a dispenser means is defined as any means which both (a) contains or holds the unvolatilized compound or compounds used to produce the vapor of the attractant and (a) releases the compound or compounds in the vapor phase.

A dispensing means may take several forms. For example, it may be as simple as a fencepost or tree, wherein a formulation to produce the volatilized compounds, mixture or volatilized I and II is painted, sprayed, or otherwise applied to the fencepost or tree, for release into the ambient area. Other dispensing means include an adsorbent material such as cotton or paper which both holds and releases I or II. In general, however, a dispensing means will comprise a reservoir for holding an amount of a compound either within a space or a polymeric matrix, with the release into the atmosphere controlled by a permeable wall or membrane or by a small opening surrounded by an impermeable wall or membrane. Examples of dispensers include a reservoir and polyethylene cap within a trap as described in the Example, below. Further examples of dispensers include polymer caps, bubbles, hollow fibers, hollow tubes or tubing which release compounds through the walls, capillary tubing which release compounds out of an opening in the tubing, polymeric blocks of different shapes which release compounds out of the polymer matrix, membrane systems which hold the chemicals within an impermeable container and release them through a measured permeable membrane, and combinations of the foregoing. Examples of other dispensing means are polymer laminates, polyvinyl chloride pellets, microcapillaries, and Shunitzu rope. Another dispensing means includes using microencapsulation techniques to encapsulate each compound used to produce the vaporized compound, mixture or vapor blend.

In one aspect, 3-methyl-1-butanol, 3-methyl-1-pentanol or mixtures thereof are placed in a dispensing means.

In another aspect, the attractant combination of I and II are formulated in a dispensing means. In one embodiment, I and II are formulated as a mixture and placed in the dispensing means. In another embodiment, the compound that produces acetic acid vapor is provided in a first dispenser and the compound or compounds that produce vapor of component II is placed in a second dispenser, and the two dispensers are placed in sufficient proximity to one another to form a volatilized blend of I and II in the surrounding atmosphere. The first and second dispensers may optionally be attached or fused to form one device or unit that releases I and II to form the vapor blend. Alternatively, I and II may be formulated separately, for example, placing acetic acid in a drowning solution and placing a compound of group II in a polyethylene cap as described in the Example, below. In still another embodiment, the vapor blend of I and II is provided by 3-methylbutyl acetate which releases acetic acid and 3-methyl-1-butanol vapors as a blend.

Effective odorant amounts (acetic acid, 3-methyl-1-butanol, 3-methyl-2-butanol, or 3-methyl-1-pentanol released individually as a vapor into air) are most readily defined as weight amounts released per unit time from a formulation, dispenser, bait or trap. The broad range of release rates is that which is an effective attractant for the target moth. An effective release rate range for acetic acid is at least about 10 µg per hour. A preferred release rate range of acetic acid is from about 50 µg per hour to 1000 µg per hour. An effective release range for 3-methyl-1-butanol, 3-methyl-2-butanol, or 3-methyl-1-pentanol is at least about 50 µg per hour. A preferred release rate range is about is about 50 µg per hour to 2000 µg per hour.

Controlled release of the compounds may also be effected in part through the addition of an extender such as mineral oil, which will reduce the rate of volatilization of the odorants out of the dispenser.

Factors such as moth species present, moth population density, and environmental factors influencing moth foraging behavior (e.g., temperature, wind velocity, rain, time of day and seasonality) will influence the response of moths to the attractants of the invention and the actual number of moths attracted. The amounts of compound or compounds in a particular set of circumstances that will provide release rates within an effective range can be readily determined by dose response field tests as described in the Example, below.

The lures may be combined with feeding stimulants to provide baits for moths, particularly pestiferous noctuid species. Toxicants may also be added to provide poisoned baits, as discussed in detail below. Other compounds and materials may be added to a formulation, lure, bait or trap provided they do not substantially interfere with the attractancy of the attractant vapor composition of the invention. Whether or not an additive substantially interferes with the attractant activity can be determined by standard test formats, involving direct comparisons of efficacy of the attractant without an added compound and the attractant with an added compound. Reductions in attractancy, such as reduced captures of moths in traps baited with the attractant with the additive, may be determined with standard statistical analyses.

Trapping Systems. The attractants of the invention may be used as detecting agents, surveying agents, monitoring agents, or control agents for the moths. Conveniently, the attractants are dispensed within a trapping means to attract and trap moths. A trapping system for monitoring or controlling moths includes a trapping means, and a dispenser means located within the trapping means which provides an effective attractant amount (a) of vaporized 3-methyl-1-butanol, 3-methyl-1-pentanol or mixtures thereof, or (b) of a vapor blend of vapor of (I) acetic acid and vapor of (II) one or more compounds selected from the group consisting of 3-methyl-1-butanol, 3-methyl-2-butanol, and 3-methyl-1-pentanol. A trapping means is any device for catching insects, particularly, noctuid moths. These include for example, the Trappit™ dome trap by Agrisense, LIQUIDA-TOR Trap by Phero Tech Inc., Yellow Jacket Wasp Trap by Oak Stump Farm (U.S. Pat. No. 4,794,724), the Pherocon ® trap by Zoecon, Inc., and the Universal moth trap or UNI-TRAP.

A preferred trap for the combination attractant of the invention is one which has a mixing chamber wherein vapors of I and II form a blend and the vapor blend of I and II exits the trap chamber and attracts moths to the chamber where they are trapped. Compounds I and II that produce the attractant vapor blend may be presented as a mixture or in separate dispensers within the trap. Acetic acid and a compound of II may be added directly to a drowning solution that can be used in a trap, with the attractant blend emanating from the drowning solution. This drowning solution may optionally contain additional materials that aid in the capture and killing of attracted moths, such as detergents or wetting agents, clays, dyes and toxicant, as long as such additives do not substantially interfere with the attractiveness of the attractant blend of the invention.

For dry traps, in which attracted moths are killed by toxicant or insolation, other formulation methods may be used as known in the art.

Means for Controlling Moths. The attractants of the invention are useful for control of noctuid moths when used in concert with means for controlling moths. Control of moths may be carried out as known in the art, including (a) by capturing the moths in traps, (b) by capturing moths in a trap and killing the moths, for example, by means of a drowning solution or pesticide for moths, or (c) by use of toxicants, pesticides or chemosterilants, (d) by use of poisoned bait, e.g., the combination of a feeding stimulant and toxicant, or (e) by use of pathogens, for example, by bringing the attracted moths into contact with pathogens or by incorporating pathogens.

Insecticides or toxicants for moths include compounds such as methomyl, dimethyl (2,2,2-trichloro-1-hydroxyethyl) phosphonate, 2,2-dichlorovinyl dimethyl phosphate, and 1,2-dibromo-2,2-dichloroethyl dimethyl phosphate. Other toxicants are selected from the group consisting of organophosphorus toxicants, carbamates, inorganic toxicants, and insect growth regulators.

A toxicant may be in a powdered form, may be a vapor released from a dispenser or may be incorporated into a bait whereby the moth becomes attracted to the toxicant and becomes contaminated or infected (in the case of pathogens) with the toxicant or ingests the toxicant. Toxicants which may be useful in this invention are those which will not adversely affect the attractiveness of the attractants of the invention. A variety of matrix materials may also be employed as a carrier for the toxicant and the attractant.

Combination of attractant and visual target. For purposes of trapping or baiting, visual targets may be used to focus close range orientation of attracted moths, either to facilitate their being captured in traps or to facilitate their arrival on a bait. For example, some species of moths are optimally attracted to bright white targets and others to small dark targets.

Kits and packaged attractants. The invention is also directed to kits. In one aspect the kit includes a trap and a lure for use within the trap and which provides the attractant. The kit may also include a drowning solution for some trap designs. Another kit includes at least two components, wherein one component is acetic acid and another component is one or more compounds selected from the group consisting of 3-methyl-1-butanol, 3-methyl-2-butanol, and 3-methyl-1-pentanol and means for dispensing the compounds to provide the attractant blend of the invention. The components may be in a drowning solution, formulation (chemical matrix to hold and release one or more attractant chemicals), dispenser or bait as discussed above. Drowning solutions, formulations, dispensers and controlled release devices may be rechargeable with a measured amount of I and II.

A bait kit may contain the compounds to provide the attractant compound, combination or blend of the invention in a matrix or suitable carrier for moths to contact and remove. The bait may also contain additives, such as feeding stimulants, toxicants, extenders, antioxidants, and/or UV adsorbers.

The invention is also directed to a packaged attractant which comprises at least two components, wherein one component is one that provides acetic acid vapor and another component is one or more compounds selected from the group consisting of 3-methyl-1-butanol, 3-methyl-2-butanol, and 3-methyl-1-pentanol, wherein the components are packaged in separate containers and wherein the packaged attractant further comprises instructions for producing a volatilized blend of the two components when the components are released from the containers.

USES OF THE INVENTION

The chemical attractant is useful in detecting, surveying, monitoring, or controlling populations of moths, primarily in the family Noctuidae. In the family Noctuidae, there are many species of cutworms, armyworms, fruitworms, and others that cause severe losses of vegetable and fruit, as well as forage, and fiber crops. The invention finds particular use for detecting, surveying, monitoring, and controlling these pestiferous species. Examples of noctuid moth species that are major crop pests include *Lacanobia subjuncta*, bertha armyworm, spotted cutworm, fall armyworm (*Spodoptera frugiperda*), beet armyworm (*Spodoptera exigua*), yellow striped armyworm (*Spodoptera ornithogalli*), Western yellowstriped armyworm (*Spodoptera praefica*), Southern armyworm (*Spodoptera eridania*), armyworm (*Pseudaletia unipuncta*), corn earworm (*Helicoverpa zea*), *Helicoverpa armigera*, *Helicoverpa peltigera*, tobacco budworm (*Heliothis virescens*), black cutworm (*Agrotis ipsilon*), cotton leafworm (*Alabama argillacea*), grass looper (*Mocis latipes*), velvetbean caterpillar (*Anticarsia gemmatalis*), forage looper (*Caenurgina erechtea*), variegated cutworm (*Peridromia saucia*), and spiny bollworm (*Earias insulana*). Additional noctuid pests of crops are set forth in *Destructive and Useful Insects. Their Habits and Control* by C. L. Metcalf, W. P. Flint, and R. L. Metcalf, McGraw Hill Book Co., N.Y. (1962), 1087 pages.

Crops with major noctuid pest problems include cotton, corn, soybean, alfalfa, cabbage (cole crops generally), mustards (including canola), apple, tomato, potato, lettuce, asparagus, sugar beets, sorghum, sugar cane, and lettuce.

When used as a detection, survey, or monitoring agent, traps are baited with the novel attractant of the invention and the catch tabulated to determine size and location of infestation. Economic use of appropriate control agents can then be determined.

As discussed above, use of the attractants as control agents can be carried out in several ways. The attractant may be placed within a trap which allows the insects to enter but prevents their exit. In this manner, the foraging power of the colony is reduced thereby achieving some degree of control over the colony. Another method is to use the attractant to attract the moths to suitable substrates and subsequently or simultaneously expose the insects to insecticides which control the moths. An effective amount of the insecticide, toxicant or other bioactive chemical or material is used, that is, an amount sufficient upon contact or ingestion to kill the moth, to render it impaired sufficiently to be trapped, drowned, or insolated, or to disrupt neural or other physiological functions to prevent essential colony functions or reproduction. An effective amount of a pathogen or disease organism is used, that is, an amount sufficient upon contact or ingestion or carried by the moth, to kill the moth or initiate an epizootic within the population. Insecticides can be used in traps baited with the attractant, thereby minimizing the dissemination of the insecticide and contamination of foods and the environment. Chemosterilants can be used in conjunction with the composition to attract and sterilize moths.

Another method to control the moths using the composition of the invention is to detect the location and boundaries of localized moth populations, and then employ in the area biological control agents.

EXAMPLE

The following example is intended only to further illustrate the invention and are not intended to limit the scope of the invention which is defined by the claims.

The following example describes studies assessing attractants of the invention for three species of Noctuidae that are pests in the Yakima Valley of Washington.

Materials and Methods. The Trappit™ dome trap (Agrisense, Fresno, Calif.) was used in all tests. Two hundred ml of a drowning solution was used in the reservoir of all traps. This solution was 200 ml water, 25 $\mu$l of detergent, 50 $\mu$l yellow, 25 $\mu$l blue, and 60 $\mu$l red food dyes (McCormick, Hunt Valley, N.J.), and 20 mg clay. Acetic acid, when tested, was added to the drowning solution as a percent of the solution. Alcohols tested were loaded in polyethylene caps (No. 60975D-3, Kimball Glass, Vineland, N.J.) that were impaled on a push pin glued to the inside of the top of the trap. Traps were serviced two or three times per week depending on weather conditions, and the drowning solution with or without acetic acid was replaced weekly. Alcohols in polyethylene caps were replaced monthly.

All experiments were conducted in commercial apple and pear orchards. Traps were hung from tree branches at 1.5 to 2 m above ground, with 10 m between traps within a block and 10 m between adjacent blocks.

Experiment Overview. Four trapping experiments were conducted in apple and pear orchards in the Yakima Valley during the summer of 1998. An initial experiment compared captures of pest moths in traps baited with the combination of acetic acid and 3-methyl-1-butanol to acetic acid alone and to fermented molasses solution. The second experiment was a comparison of the attractiveness of the combination of acetic acid and 3-methyl-1-butanol with varying percentages of acetic acid in the drowning solution. The third experiment was a comparison of the attractiveness of the combination of acetic acid and 3-methyl-1-butanol with varying doses of the 3-methyl-1-butanol in the cap. The fourth experiment was a test of possible synergism or enhancement of acetic acid with 3-methyl-1-butanol and acetic acid with 3-methyl-1-pentanol and a comparison of the two alcohols.

Trap catch data for each species was subjected to an ANOVA and means were separated by Duncan's New Multiple Range Test for the first and fourth experiments. Linear regression was used to analyze trap data from the second and third experiments to determine if their was a significant relationship between concentration (acetic acid) or dose (3-methyl-1-butanol) and captures of moths in traps.

Results Overview. In the first experiment the increased response of both sexes of all three species to the combination attractant of the invention was evident in comparison to acetic acid alone and the superiority of the attractant blend in comparison to fermented molasses solution was also apparent. In the second experiment the increased attractiveness of the blend to *L. subjuncta* and bertha armyworms in comparison to 3-methyl-1-butanol alone was demonstrated, and in the third experiment the increased attractiveness of the blend to the same to species in comparison to acetic acid alone was demonstrated. The greater activity of the combination of chemicals versus the individual components was again demonstrated in the fourth experiment as was the increased attractiveness of the combination of acetic acid and 3-methyl-1-pentanol in comparison to acetic acid alone or 3-methyl-1-pentanol alone to *L. subjuncta* and the spotted cutworm.

Results of Experiment 1 and combined results of Experiments 2 and 3 indicate that acetic acid and 3-methyl-1-butanol act synergistically as an attractant for these moths that is greatly enhanced relative to the separate components.

Throughout the experiments, which lasted throughout the 1998 field season and through both generations of both species of moths, these chemicals consistently attracted females as well as males of *L. subjuncta, M. configurata* (bertha armyworm), and *X. c-nigrum* (spotted cutworm). Such a lure is useful in tracking reproductive activities such as female egg laying and may be used to monitor population densities.

Experiment 1. Traps were baited (1) with 0.25% acetic acid in the drowning solution, (2) with 0.5% acetic acid in the drowning solution and one ml of 3-methyl-1-butanol in a polyethylene cap, or (3) with 200 ml of a 10% solution of molasses in water. A randomized complete block design was used, with 4 blocks set up in early May. Traps were maintained through May and June and again in August.

Results of Experiment 1. In the first experiment, numbers of males and numbers of females of *Lacanobia subjuncta* captured in traps baited with acetic acid and 3-methyl-1-butanol were significantly greater than numbers captured in traps baited with acetic acid or with molasses (ANOVA F=31.5 for females, 29.1 for males, df=387) (FIG. 1A). There was no difference between catches of male or female *L. subjuncta* captured in traps baited with acetic acid versus molasses. Overall, the numbers of males and females captured were similar for all treatments. Numbers of males and numbers of females of *L. subjuncta* captured in traps baited with acetic acid and 3-methyl-1-butanol were significantly greater than numbers captured in traps baited with acetic acid or with molasses (ANOVA F=31.5 for females, 29.1 for males, df=387) (FIG. 1A). There was no difference between catches of male or female *L. subjuncta* captured in traps baited with acetic acid versus molasses. Overall, the numbers of males and females captured were similar for all treatments.

Figure 1B:
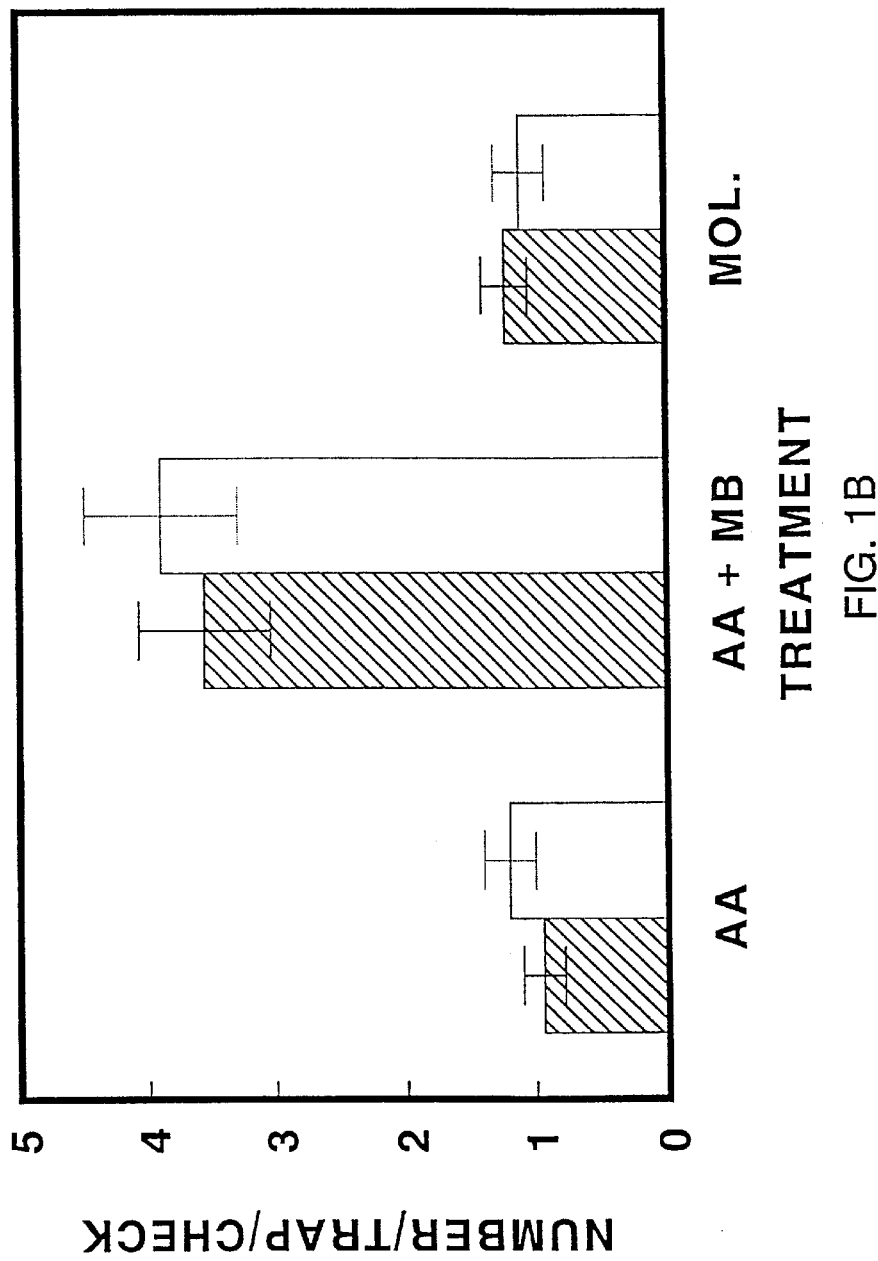
Figure 1C:
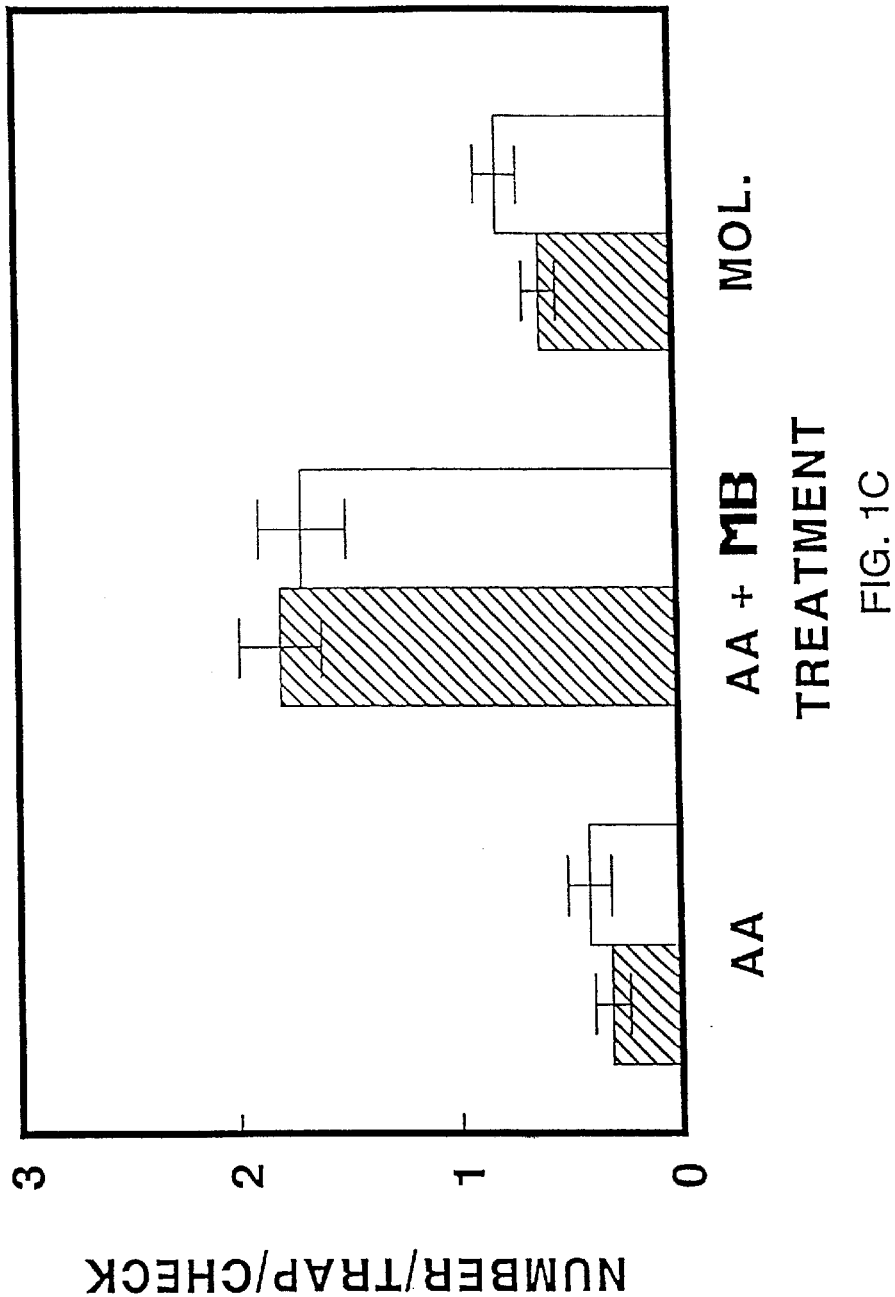

Numbers of males and numbers of females of *M. configurata* captured in traps baited with acetic acid and 3-methyl-1-butanol were significantly greater than numbers captured in traps baited with acetic acid or with molasses (ANOVA F=19.0 for females, 16.7 for males, df=344) (FIG. 1B). There was no difference between catches of male or female *M. configurata* captured in traps baited with acetic acid versus molasses. Overall, the numbers of males and females captured were similar for all treatments.

Numbers of males and numbers of females of *X. c-nigrum* captured in traps baited with acetic acid and 3-methyl-1-butanol were significantly greater than numbers captured in traps baited with acetic acid or with molasses (ANOVA F=37.6 for females, 20.4 for males, df=374) (FIG. 1B). There was no difference between catches of female *X. c-nigrum* captured in traps baited with acetic acid versus molasses. However, numbers of male *X. c-nigrum* in traps baited with molasses were significantly higher than numbers captured in traps baited with acetic acid. Overall, the sex ratio captured was near 1:1 for all treatments.

Experiment 2. Traps were all baited with one ml of 3-methyl-1-butanol in a polyethylene cap and with either no acetic acid in the drowning solution or with 0.008, 0.03, 0.125, 0.5, or 2% glacial acetic acid by volume in the 200 ml of drowning solution. A randomized complete block design was used, with 4 blocks set up in late July, with each of the 6 treatments represented within each block. This experiment was maintained through August and early September.

Figure 2:
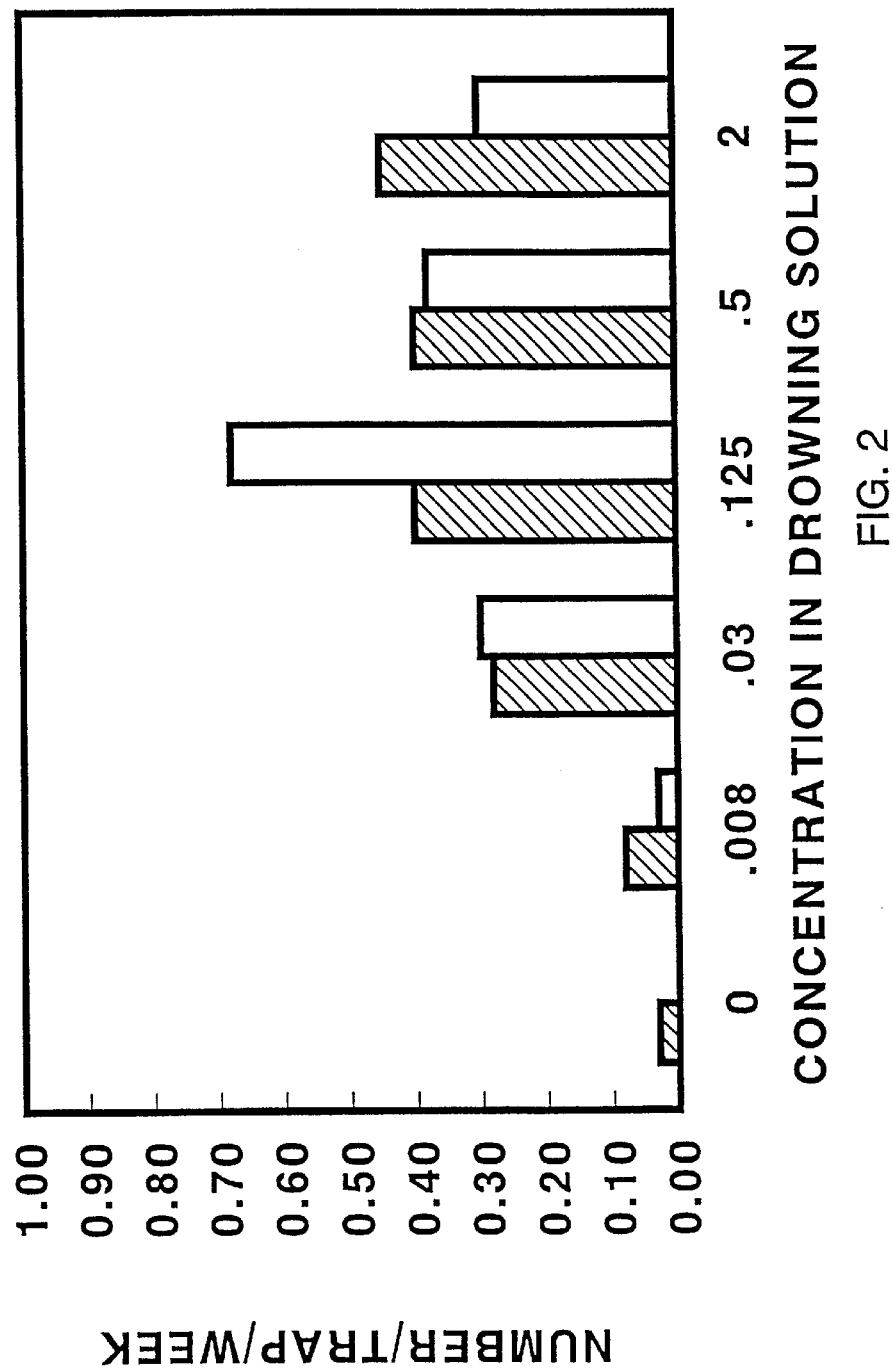
FIG. 2 shows the mean numbers of *Lacanobia subjuncta* (LS) and bertha armyworm moths (BAW) captured in traps baited with one ml of 3-methyl-1-butanol and different concentrations of acetic acid in the trap's drowning solution.

Results of Experiment 2. Numbers of moths captured in traps were suitable for statistical analyses for *L. subjuncta* (LS) and bertha armyworm (*M. configurata*) (BAW). Spotted cutworms were not abundant in that study plot. Numbers of *L. subjuncta* captured in traps baited with the combination of 3-methyl-1-butanol and acetic acid increased significantly with increasing concentrations of acetic acid over the range tested (up to 2%) (FIG. 2). Numbers of moths captured in traps baited with 3-methyl-1-butanol either alone or in combination with acetic acid at a concentration of 0.008% captured nearly no moths. Numbers of bertha armyworms captured in traps baited with the combination of 3-methyl-1-butanol and acetic acid increased up to the 0.125% acetic acid concentration, which had the highest trap catch. Captures of moths were decreased at 0.5 and 2% acetic acid in the drowning solution (FIG. 2). Nearly no bertha armyworm moths were captured in traps baited with 3-methyl-1-butanol alone or in traps baited with 3-methyl-1-butanol in combination with acetic acid at a concentration of 0.008%.

Experiment 3. Traps were all baited with 0.25% acetic acid in the drowning solution and either 0, 12.5, 25, 50, or 100% 3-methyl-1-butanol in one ml of a mixture of 3-methyl-1-butanol and mineral oil. A randomized complete block design was used with each of the 5 treatments represented within each block. This experiment was set up in late July and was maintained through early September.

Figure 3:
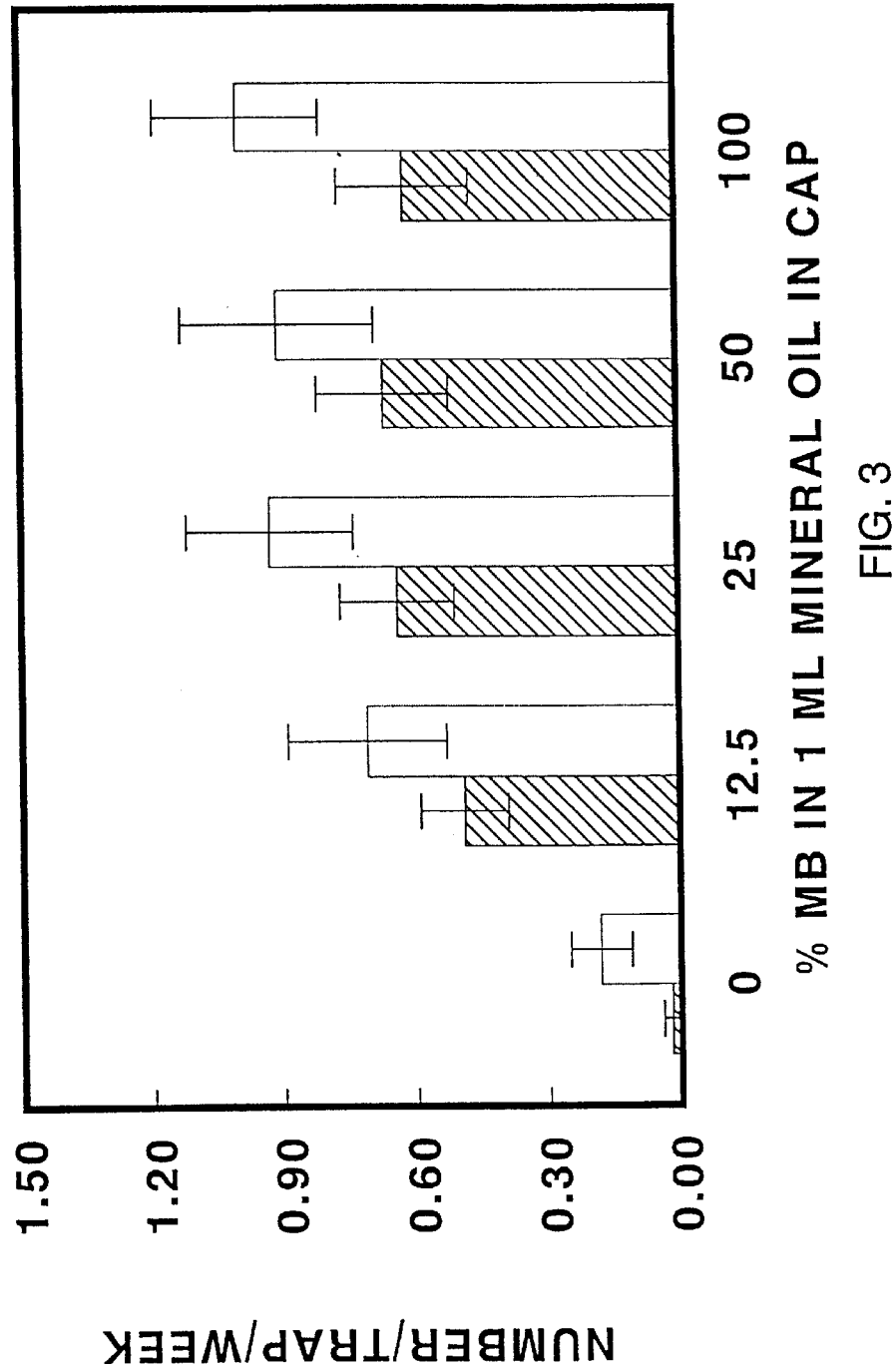
FIG. 3 shows the mean numbers of *Lacanobia subjuncta* (LS) and bertha armyworm moths (BAW) captured in traps baited with 0.25% acetic acid in the drowning solution and with varying amounts of 3-methyl-1-butanol mixed with mineral oil in a polyethylene cap.

Results of Experiment 3. Numbers of moths captured in traps were suitable for statistical analyses for *L. subjuncta* (LS) and bertha armyworm (*M. configurata*) (BAW). Spotted cutworms were not abundant in that study plot. Numbers of *L. subjuncta* and numbers of bertha armyworms captured in traps baited with the combination of acetic acid and 3-methyl-1-butanol did not increase significantly with increasing doses of 3-methyl-1-butanol in caps (FIG. 3). For both species, numbers of moths captured in traps baited with acetic acid and 3-methyl-1-butanol at 12.5, 25, 50, and 100% in the cap were similar. At each dose of 3-methyl-1-butanol, numbers of both species of moths in traps were significantly greater than numbers in traps baited with acetic acid alone by student's t test.

Experiment 4. Traps were either unbaited (control) or were baited with 0.25% acetic acid in the drowning solution (acetic acid), with 0.25% acetic acid in the drowning solution and one ml of 3-methyl-1-butanol in a polyethylene cap, with 0.25% acetic acid in the drowning solution and one ml of 3-methyl-1-pentanol in a polyethylene cap, with one ml of 3-methyl-1-butanol in a cap, or with one ml of 3-methyl-1-pentanol in a cap. A randomized complete block design was used with each of the 6 treatments represented within each block. This experiment was set up in late July and was maintained through the first of September.

Results of Experiment 4. Numbers of *L. subjuncta* (Lacanobia) captured were highest in traps baited either with the combination of acetic acid and 3-methyl-1-butanol or with the combination of acetic acid and 3-methyl-1-pentanol (FIG. 4), although they were not significantly higher than those caught in traps baited with 3-methyl-1-pentanol alone. Numbers of *L. subjuncta* captured in traps baited with 3-methyl-1-butanol or with 3-methyl-1-pentanol or with acetic acid alone were similar, and were significantly higher than the unbaited traps.

Figure 4:
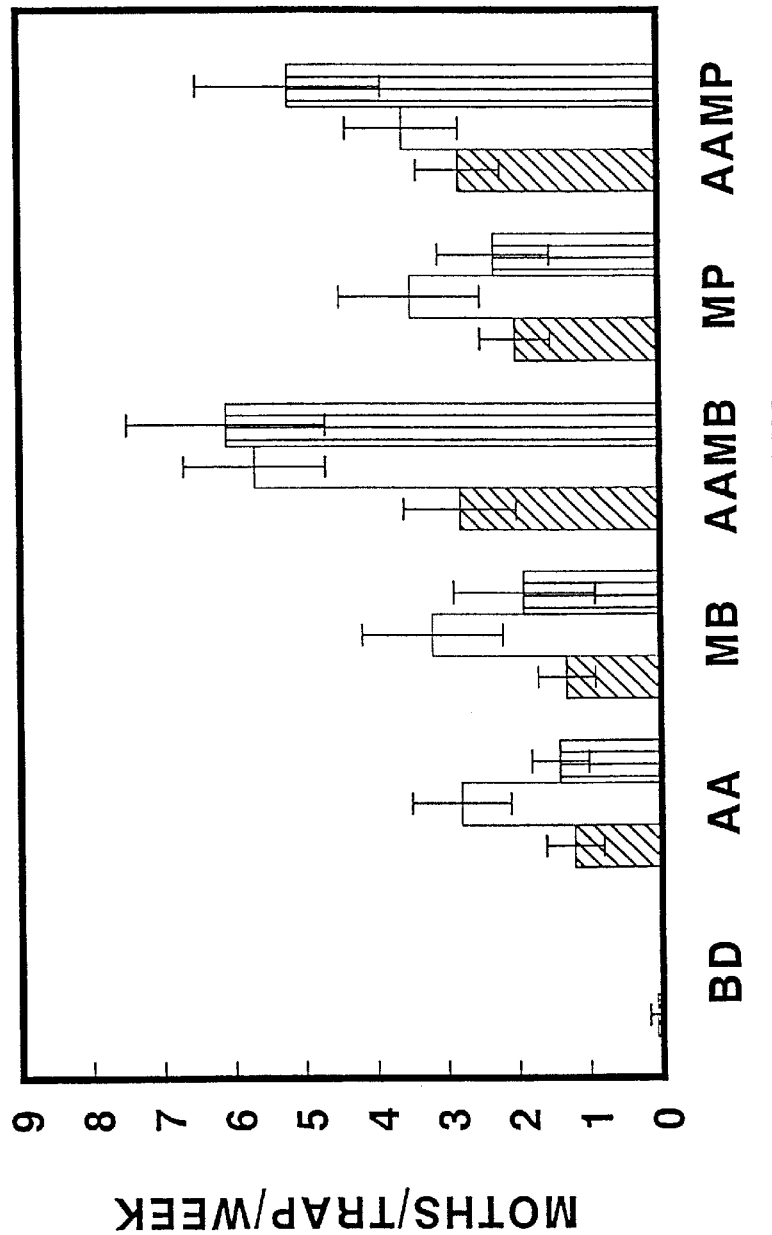
FIG. 4 shows the mean numbers of *Lacanobia subjuncta*, bertha armyworm moths (*M. configurata*), and spotted cutworm moths (*X. c-nigrum*) captured in unbaited traps (blank) or in traps baited with 0.25% acetic acid (AA) in the drowning solution, with one ml of 3-methyl-1-butanol (MB) or one ml of 3-methyl-1-pentanol (MP) or combinations of acetic acid and the alcohols (AAMB and AAMP).

Numbers of bertha armyworms (*M. configurata*) (bertha) captured were highest in traps baited with the combination of acetic acid and 3-methyl-1-butanol (FIG. 4). Numbers of *M. configurata* captured in traps baited with 3-methyl-1-butanol alone, 3-methyl-1-pentanol alone, acetic acid alone or 3-methyl-1-pentanol with acetic acid were similar, and were significantly higher than the unbaited traps.

Numbers of *X. c-nigrum* captured were highest in traps baited either with the combination of acetic acid and 3-methyl-1-butanol or with the combination of acetic acid and 3-methyl-1-pentanol (FIG. 4). Numbers of *X. c-nigrum* captured in traps baited with 3-methyl-1-butanol or with 3-methyl-1-pentanol or with acetic acid alone were similar, and were significantly higher than the unbaited traps.

It is understood that the foregoing detailed description is given merely by way of illustration and that modification and variations may be made within, without departing from the spirit and scope of the invention.

What is claimed is:

1. A method for attracting male and female noctuid moths, which comprises placing in an area where said moths are to be attracted, a dispenser means which provides
   (a) an effective noctuid moth attractant amount of vapor comprising 3-methyl-1-pentanol, or
   (b) an effective noctuid moth attractant amount of a vapor blend comprising an attractant component which comprises vapor of (I) acetic acid and vapor of (II) one or more compounds selected from the group consisting of 3-methyl-2-butanol and 3-methyl-1-pentanol.

2. The method of claim 1 wherein said vapor blend is provided by a dispenser means which contains a mixture of (I) acetic acid and (II) one or more compounds selected from the group consisting of 3-methyl-2-butanol and 3-methyl-1-pentanol.

3. The method of claim 1 wherein said vapor blend is provided by a dispenser means which comprises a first dispenser which contains (I) acetic acid and a second dispenser which contains (II) one or more compounds selected from the group consisting of 3-methyl-2-butanol and 3-methyl-1-pentanol, wherein said first and second dispensers are in proximity effective to provide said vapor blend of I and II.

4. The method of claim 1 wherein said acetic acid vapor in said vapor blend is provided by aqueous acetic acid, concentrated acetic acid or ammonium acetate.

5. The method of claim 1 wherein said dispenser means is located within a trapping means for said moths.

6. The method of claim 1 which further includes a means for controlling said moths.

7. A lure for attracting male and female noctuid moths which comprises a dispenser means which provides a vapor blend comprising a synthetic attractant component which comprises vapor of (I) acetic acid and vapor of (II) one or more compounds selected from the group consisting of 3-methyl-2-butanol and 3-methyl-1-pentanol, wherein said dispenser means comprises a first dispenser which contains I and a second dispenser which contains II, wherein said first and second dispensers arc in sufficient proximity effective to provide said vapor blend of I and II, and wherein said lure provides an effective noctuid moth attractant amount of said vapor blend.

8. The lure of claim 7 which further includes a means for controlling said moths.

9. A trapping system for monitoring or controlling male and female noctuid moths, which comprises a trapping means, and a dispenser means located within said trapping means which provides an effective noctuid moth attractant amount of a vapor blend comprising an attractant component which comprises vapor of (I) acetic acid and vapor of (II) one or more compounds selected from the group consisting of 3-methyl-2-butanol and 3-methyl-1-pentanol.

10. The trapping systeni of claim 9 wherein said dispenser means contains a mixture of I and II.

11. The trapping system of claim 9 wherein said dispenser means comprises a first dispenser which contains I and a second dispenser which contains II, and wherein said first and second dispensers provide said vapor blend of I and II.

* * * * *